United States Patent [19]

Hardtmann et al.

[11] 4,221,797
[45] Sep. 9, 1980

[54] DIHYDROQUINOLINE-ONE DERIVATIVES

[75] Inventors: Goetz E. Hardtmann, Morristown; Gary M. Coppola, Mt. Olive, both of N.J.

[73] Assignee: Sandoz, Inc., E. Hanover, N.J.

[21] Appl. No.: 933,421

[22] Filed: Aug. 14, 1978

[51] Int. Cl.$^2$ ..................... A61K 31/47; C07D 215/56
[52] U.S. Cl. .................................. 424/258; 546/153; 546/155
[58] Field of Search ............... 260/287 AN; 424/258; 546/153, 155

[56] References Cited

U.S. PATENT DOCUMENTS

| | | | |
|---|---|---|---|
| 4,070,468 | 1/1978 | Hardtmann et al. | 424/258 |
| 4,107,310 | 8/1978 | Allais et al. | 546/156 |
| 4,123,536 | 10/1978 | Connor et al. | 546/156 |

FOREIGN PATENT DOCUMENTS 828690 3/1975 Belgium .
1121411 7/1968 United Kingdom .

OTHER PUBLICATIONS

Coutts et al., "J. Chem. Soc." (1962), pp. 2518–2521.

*Primary Examiner*—Nicholas S. Rizzo
*Assistant Examiner*—David E. Wheeler
*Attorney, Agent, or Firm*—Gerald D. Sharkin; Richard E. Vila; Frederick H. Weinfeldt

[57] ABSTRACT

The compounds are amino- or cyano-bearing dihydroquinolines, which have either of the combinations of (a) 2-amino, 3-carboxylic and 4-oxo functions, or (b) 2-oxo, 3-cyano and 4-hydroxy functions, and may be optionally substituted at 1 or 2 of the 5, 6, 7 or 8 positions, eg 1-allyl-2-amino-1,4-dihydro-6,7-dimethoxy-4-oxo-quinoline-3-carboxylic acid ethyl ester, and 1-allyl 3-cyano-1,2-dihydro-4-hydroxy-6,7-dimethoxy-2-oxo-quinoline. The compounds are useful as pharmaceuticals.

11 Claims, No Drawings

DIHYDROQUINOLINE-ONE DERIVATIVES

The invention relates to chemical compounds which are dihydroquinoline derivatives, to their preparation and to their use as pharmacological agents, particularly as anti-allergic agents, and to pharmaceutical compositions containing said compounds.

The compounds of the invention (compounds I) are dihydroquinoline derivatives which may be individually represented by the formula Ia:

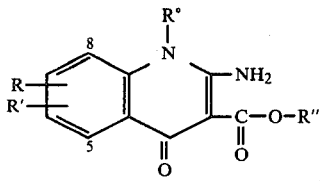

wherein
$R^o$ is hydrogen, alkyl of 1 to 6 carbon atoms, alkenyl of 3 to 6 carbon atoms, alkynyl of 3 to 6 carbon atoms, cycloalkyl of 3 to 6 carbon atoms, cycloalkylalkyl in which the cycloalkyl is of 3 to 6 carbon atoms and the alkyl portion is of 1 or 2 carbon atoms, or

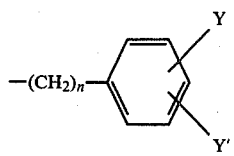

in which
n is 0 or 1,
Y and Y' are, independently, hydrogen, halo of atomic weight of from 18 to 80, i.e., fluoro, chloro or bromo, alkyl of 1 to 3 carbon atoms, alkoxy of 1 to 3 carbon atoms or trifluoromethyl, provided that the unsaturation in any alkenyl or alkynyl is other than on the alpha carbon atom;
R and R' are independently hydrogen, fluoro, chloro, bromo, alkyl of 1 to 4 carbon atoms, alkoxy of 1 to 4 carbon atoms, nitro or trifluoromethyl; provided that only one of R and R' can be nitro or trifluoromethyl; or R and R' together form 6,7-methylenedioxy; (preferably R and R' being other than hydrogen, and more preferably at the 6- and/or 7-positions); and
R" is either alkyl of from 1 to 4 carbon atoms, or M, wherein M is either hydrogen or a cation; and by the formula Ib:

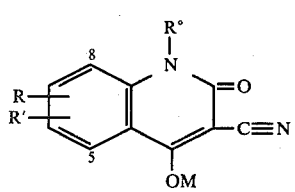

in which $R^o$, R, R' and M are as defined above.

Compounds Ia in which R" is alkyl and Compounds Ib are obtainable concurrently in a process (a) by reacting an isatoic anhydride compound of formula II:

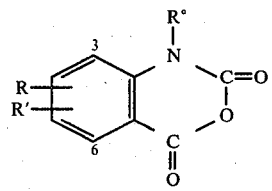

in which R, R' and $R^o$ are as defined above; with a metallo cyano-acetate compound of the formula III:

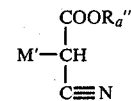

in which $R_a"$ is the same as R" as defined above when it is alkyl, and M' is an alkali metal, eg. sodium.

The preparation of compounds I in accordance with process (a) is suitably carried out in an inert organic solvent, e.g., dimethylacetamide, and at a temperature of from 0° C. to 150° C., preferably 60° C. to 130° C., followed, if necessary or desired, by neutral or acid hydrolysis to obtain the desired compound Ib from any 4-alkali metal salt thereof initially produced.

The compounds of the formula III may be produced from the corresponding cyanoacetate esters of the formula IIIa:

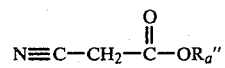

in which $R_a"$ is as defined, above by reaction with a strong alkali base, e.g. sodium hydride, in an inert organic solvent, e.g., dimethylacetamide. The strong base may be employed in the form of a solution or suspension for ease of handling, e.g. in mineral oil or in paraffin. The reaction is carried out under essentially moisture-free conditions as are conventionally practiced in carrying out "Grignard-type" reactions. It is particularly convenient to prepare a compound III from its corresponding compound IIIa, and then use it in situ, ie., employ the resulting compound III in a process (a) without recovering it beforehand.

It will be appreciated from the above-described process (a), that compounds Ia and Ib are obtained as co-products. The two classes of compounds, however, are not necessarily obtained thereby in equal proportions, and variations in reaction conditions will render one or the other in better yield at the expense of the other, as may be desired.

The compounds of the formula Ia in which R" is hydrogen may be obtained by hydrolyzing a corresponding compound Ia in which R" is alkyl. For example, a compound Ia in which R" is alkyl, particularly in which R" is a highly labile alkyl group, desirably t-butyl, may be subjected to mild temperature but otherwise conventional acid catalysed decomposition. In such reaction the temperature conditions are controlled, e.g., from minus 20° C. to 60° C., preferably from minus 10° C. to 35° C., in order to avoid decarboxylation of the compounds I. Acids of known conventional types for such acid decompositions may be employed. Representative such acids include sulfuric acid, hydrochloric acid and perchloric acid, preferably the latter. The decomposition is suitably carried out in conventional solvent systems for such decompositions, such as a water miscible non-hydroxylic organic solvent such as acetonitrile, tetrahydrofuran and the like, preferably acetonitrile, such solvent system preferably containing only small amounts of water. The compounds of the formula Ia in which R'' is a cation may be prepared from the free acids (R''=H) by treatment with a base or by basic hydrolysis of the esters, in accordance with known procedures.

The compounds Ib in which M=H, have an acidic 4-hydroxy group which may be neutralized to provide corresponding compounds in salt form. Such salt forms of compounds Ib (ie in which M is an equivalent of a cation) are preferably prepared from free acid forms of compounds Ib by procedures well known in the art, e.g., by treating with a base, such as dilute sodium hydroxide, in a water miscible solvent.

It will, therefore, be understood that compounds I can exist in the form of salts, and such are contemplated as within the scope of this invention. Those compounds I in which any M is an equivalent of a cation which forms a pharmaceutically acceptable salt form are herein designated compounds I'. Other salt forms of Compounds I which are not pharmaceutically acceptable may be prepared and ultimately converted to pharmaceutically acceptable forms by conventional means, for such purposes as ease of recovery or convenience in handling.

Reagents and starting materials employed in preparing Compounds I of this invention eg. Compounds II and IIIa, are either known per se or where not known, may be prepared from known materials by adaptation of procedures established for preparing the known compounds.

Recovery and refining of Compounds I may be effected by conventional techniques such as crystallization precipitation, vacuum distillation and the like. The particular physical properties of the individual compounds I, and particularly their inherent acidic natures, may be relied upon advantageously in recovery procedures, such as in separating coproducts of process (a). For example, since a compound Ia in which R'' is alkyl is relatively neutral, while its corresponding coproduct Ib in which M=H is slightly acidic, a basic aqueous washing will preferentially extract such Compound Ib from a reaction mixture also containing the corresponding Compound Ia.

As regards the compounds I generally, there is a preference that the same have one or both of the following features: (A) $R^o$ is alkyl or alkenyl, more preferably allyl; and (B) R and R' each represent alkoxy, particularly 6,7-dialkoxy, more preferably 6,7-dimethoxy.

STATEMENT OF UTILITY

The compounds of formula I', (whether in ester, free acid or pharmaceutically acceptable salt form) are useful because they possess disodium chromoglycate (DSCG)-like activity, in particular histamine release inhibiting activity, and are therefore useful in the treatment of allergic conditions, such as allergic asthma, as indicated in the passive cutaneous anaphylaxis test in the rat. Female rats (180–200 g) are sensitised by subcutaneous administration of 1 mg of egg albumin (Merck Nr. 967) and 200 mg. Al(OH)$_3$ in 1 ml. of physiological saline and 0.5 ml. of Haemophiluspertussis vaccine (Schweizerisches Serum and Impfinstitut, Bern; Nr. 115 325; $4 \times 10^{10}$ organism/ml) intraperitoneally. Fourteen days later, the animals are exsanguinated, the blood centrifuged, the serum collected and deep frozen. The serum thus obtained (anti-serum) is injected intradermally (0.1 ml of a 1:200 diluted serum per injection site) at four sites on the backs of untreated, female rats. Twenty-four hours later each rat is administered 0.1 to 5.6 mg/kg i.v. or 0.1 to 100 mg/kg p.o. of the test compound, and either immediately or 5 to 30 minutes afterwards, in the case of intravenous administration, or 15 or 60 minutes afterwards, in the case of oral administration, afterwards egg albumin (5 mg/ml i.v.) dissolved in physiological saline containing 0.25% Evans Blue dye (Merck Nr. 3169). The egg albumin elicits a cutaneous anaphylactic reaction, the intensity of which is proportional to the extent to which the Evans Blue dye diffuses into the tissue surrounding each of the four sensitisation sites. Thirty minutes after the administration of the egg albumin, the rats are killed with ether, the underside of the skin of the back of each animal is exposed and the diameter of the area of blue dye surrounding each of the four sensitisation sites are measured. Each dose of test compound is investigated in between four and six rats and the mean diameter compared with the mean value obtained in four solvent-treated control rats. The percentage inhibition is taken as the percentage of the mean diameter in the test animals relative to the mean diameter in the controls.

The DSCG-like activity, in particular histamine release inhibiting activity, can be confirmed by inhibition of histamine release in the rat peritoneal mast cell test, basically as described by Kusner et al., J. Pharmacol. Exp. Therap. 184, 41–46 (1973), with the following modification: after sedimentation of the mast cells by centrifugation at $350 \times g$ and 4° C., the sediments are taken up in 1 ml of Hank's balanced salt solution (HBSS) (buffered to a pH of 6.9) and pooled. The resulting suspension is centrifuged, washed again with HBSS and sedimented. The thus purified mast cells are prepared as 2 ml suspensions in HBSS. To these are added either 2 ml of HBSS, to determine the spontaneous histamine release, or 2 ml of HBSS and 2.24 ug of compound 48/80 (N-methylhomoanisylamineformaldehyde condesate; a histamine liberator from Burroughs Wellcome and Co. Inc., Tuckahoe, N.Y. USA), to determine the 48/80 induced histamine release, or 2 ml of HBSS with 2.24 ug of 48/80 and from 18 to 180 ug/ml of the test compound, to determine the 48/80 induced histamine release in the presence of the test compound.

The 48/80 induced histamine release minus the spontaneous histamine release is taken as 100% histamine release. The 48/80 induced histamine release in the presence of the test compound minus the spontaneous histamine release is then compared with the 100% value to determine the percentage inhibition by the test compound. [The histamine determination is effected in conventional manner, for example as described in the above-mentioned Kusner et al. article, or in Kusner and Herzig, Advances in Automated Analysis, 429 (1971)].

For the above-mentioned use, the dosage administered will, of course, vary depending on the compound employed, mode of administration and treatment desired at a daily dosage of from about 0.5 to 100 mg/kg in animal body weight, conveniently given in divided doses two to four times daily, or in sustained release form. For the larger mammals, the total daily dosage is in the range of from about 30 to 600 mg of the compound admixed with a solid or liquid pharmaceutical carrier of conventional type, and divided dosage forms comprise 6 to 300 milligrams of the compound in admixture with a solid or liquid pharmaceutical carrier. As will be appreciated by those skilled in the art, the treatment of allergic conditions according to the invention is based on histamine release inhibition activity and is therefore essentially symptomatic. The ability to employ such compounds in the prophylactic treatment of such allergic conditions (as evident from the DSCG-like activity) is a desirable feature. However, the good oral activity relative to DSCG is a further feature.

Pharmaceutical compositions provided by the invention and useful for treating allergic conditions due to histamine release contain a compound of the formula I' as active ingredient and one or more conventional pharmaceutically acceptable carriers, and such other conventional adjuvants as may be desired or necessary. Such compositions may be in conventional orally administerable forms such as tablets, capsules, granules, dispersible powders, elixirs, syrups, suspensions and the like or in conventional parenterally administerable forms such as an injectable sterile solution, suspension or the like, e.g., a sterile injectable aqueous suspension. Such compositions including applicable unit dosage forms thereof may be prepared according to any method known in the art for the manufacture of pharmaceutical compositions. The compounds may also be administered by inhalation therapy techniques in compositions conventionally prepared and adapted for such procedures. In general, the compositions of the invention adapted for either oral, inhalation or parenteral administration may contain from 1% to 90% by total weight of active ingredient in combination with the carrier, more usually 3% to 70%. The preferred unit dosage forms are the essentially solid forms adapted for oral administration, e.g., tablets or capsules.

A representative formulation for administration 2 to 4 times a day for prophylatic treatment of allergic asthma is a capsule prepared by standard techniques to contain the following:

| Ingredients | Weight (mg.) |
|---|---|
| 1-allyl-3-cyano-1,2-dihydro-4-hydroxy-6,7-dimethoxy-2-oxo-quinoline | 50 |
| Kaolin | 210 |

The following examples are given for purposes of illustration only. All temperatures are in centigrade and room temperature is 20° to 30° C., unless indicated otherwise.

EXAMPLE 1

Part 1, preparation of 1-Allyl-3-cyano-1,2-dihydro-4-hydroxy-6,7-dimethoxy-2-oxo-quinoline (a Compound Ib)

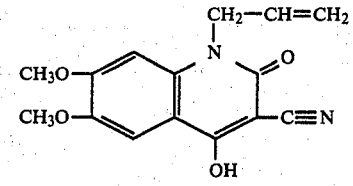

1.9 g of pentane-washed sodium hydride (50% in mineral oil) is added, with stirring, portionwise, to 4.5 g of ethyl cyanoacetate in 100 ml of dry dimethylacetamide in a vented vessel at room temperature. Hydrogen gas evolves. Stirring at room temperature is continued for an additional 30 minutes. A solution of 10 g of 1-allyl-4,5-dimethoxyisatoic anhyride in 100 ml of dry dimethylacetamide is added (in a single portion). The temperature of the reaction mixture is raised and maintained at 120° C. for a period of 3 hrs.

The reaction mixture is then cooled, placed in a rotary distillation apparatus, and the dimethylacetamide removed, under vacuum. Water is then added to the residue and the resultant aqueous mixture washed twice with dichloromethane. The aqueous mixture is then acidified with 2 N hydrochloric acid and extracted with dichloromethane. The extract is then dried over anhydrous sodium sulfate, and evaporated under vacuum to obtain an oily residue. The oily residue is then mixed with 100 ml of 10% aqueous sodium bicarbonate and washed with ethyl acetate (which wash is retained for use in Part 2, below). The aqueous phase is then acidified with 2 N hydrochloric acid, resulting in a precipitate. The precipitate is collected by filtering, then washed three times with water, dried under vacuum, and then recrystallized from methanol/ethyl acetate (m.p. 236°–239° with decomposition). Part 2, Preparation of 1-allyl-2-amino-1,4-dihydro-6,7-dimethoxy-4-oxo-quinoline-3-carboxylic acid, ethyl ester (a compound I$_a$").

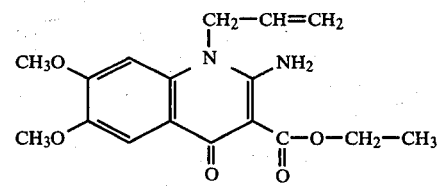

The ethyl acetate wash of the aqueous sodium bicarbonate mixture retained in Part 1, above, is dried over anhydrous sodium sulfate, then concentrated to obtain the title product m.p. 228°–231°.

EXAMPLE 2

Following the procedures of Example 1, but using in place of the 1-allyl-4,5-dimethoxyisatoic anhydride used therein, an approximately equivalent amount of a compound in Column A, (as Compounds II) there is accordingly obtained the corresponding compounds B and C (as Compounds I$_a$" and Ib), respectively:

| A | B | C |
|---|---|---|
| (a) 4,5-dimethoxy-1-propargylisatoic anhydride; | 2-amino-6,7-dimethoxy-1-propargyl-1,4-dihyrdo-4-oxo-quinoline-3-carboxylic acid, ethyl ester; | 3-cyano-6,7-dimethoxy-4-hydroxy-1-propargyl-1,2-dihydro-2-oxo-quinoline; |

-continued

| A | B | C |
|---|---|---|
| (b) 4,5-dimethoxy-1-methylisatoic anhydride; | 2-amino-6,7-dimethoxy-1-methyl-1,4-dihydro-4-oxo-quinoline-3-carboxylic acid, ethyl ester; | 3-cyano-6,7-dimethoxy-4-hydroxy-1-methyl-1,2-dihydro-2-oxo-quinoline; |
| (c) 5-chloro-1-allyisatoic anhydride | 1-allyl-2-amino-6-chloro-1,4-dihydro-4-oxo-quinoline-3-carboxylic acid, ethyl ester; | 1-allyl-6-chloro-3-cyano-4-hydroxy-1,2-dihydro-2-oxo-qiunoline; |
| (d) 1-(p-chlorophenyl) 4,5-dimethoxyisatoic anhydride | 2-amino-1-(p-chlorophenyl) 6,7-dimethoxy-1,4-dihydro-4-oxo-quinoline-3-carboxylic acid, ethyl ester; | 1-(p-chlorophenyl)-3-cyano-6,7-dimethoxy-4-hydroxy-1,2-dihydro-2-oxo-quinoline; |
| (e) 4,5-dimethoxyisatoic anhydride; | 2-amino-6,7-dimethoxy-1,4-dihydro-4-oxo-quinoline-3-carboxylic acid, ethyl ester; | 3-cyano-6,7-dimethoxy-1,2-dihydro-hydroxy-2-oxo-quinoline; |
| (f) 1-cyclohexyl-4,5-dimethoxyisatoic anhydride; | 2-amino-1-cyclohexyl-6,7-dimethoxy-1,4-dihydro-4-oxo-quinoline-3-carboxylic acid, ethyl ester; | 3-cyano-1-cyclohexyl-6,7-dimethoxy-4-hydroxy-1,2-dihydro-2-oxo-quinoline; |
| (g) 1-allyl-4,5-methylenedioxyisatoic anhydride; | 1-allyl-2-amino-6,7-methylenedioxy-1,4-dihydro-4-oxo-quinoline-3-carboxylic acid, ethyl ester; | 1-allyl-3-cyano-6,7-methylenedioxy-4-hydroxy-1,2-dihydro-2-oxo-quinoline; |
| (h) 1-isopropyl-5-methylisatoic anhydride | 2-amino-1-isopropyl-6-methyl-1,4-dihydro-4-oxo-quinoline-3-carboxylic acid, ethyl ester | 3-cyano-1-isopropyl-6-methyl-4-hydroxy-1,2-dihydro-2-oxo-quinoline; |
| (i) 1-benzylisatoic anhydride; | 2-amino-1-benzyl-1,4-dihydro-4-oxo-quinoline-3-carboxylic acid, ethyl ester; | 1-benzyl-3-cyano-4-hydroxy-1,2-dihydro-2-oxo-quinoline; |
| (j) 1-methyl-5-nitroisatoic anhydride; or | 2-amino-1-6-nitro-1,4-dihydro-4-oxo-quinoline-3-carboxylic acid, ethyl ester; and | 3-cyano-1-methyl-6-nitro-4-hydroxy-1,2-dihydro-2-oxo-quinoline; and |
| (k) 1-methylisatoic anhydride. | 2-amino-1-methyl-1,4-dihydro-4-oxo-quinoline-3-carboxylic acid, ethyl ester. | 3-cyano-1-methyl-4-hydroxy-1,2-dihydro-2-oxo-quinoline (m.p. 290°–293° from ethanol). |

EXAMPLE 3

Repeating the procedure of Example 1 but employing in place of the ethyl cyanoacetate used therein (as compound IIIa), in approximately equivalent amounts thereto of:
(a) n-propyl cyanoacetate; or
(b) t-butyl cyanoacetate;
there is accordingly obtained as Compounds Ia:
(a) the n-propyl ester of 1-allyl-2-amino-1,4-dihydro-6,7-dimethoxy-4-oxo-quinoline-3-carboxylic acid; and
(b) the t-butyl ester of 1-allyl-2-amino-1,4-dihydro-6,7-dimethoxy-4-oxo-quinoline-3-carboxylic acid.

What is claimed is:
1. 1-allyl-3-cyano-1,2-dihydro-4-hydroxy-6,7-dimethoxy-2-oxo-quinoline.
2. A method of treating allergic condition due to histamine release comprising administering to a mammal in need of such treatment an allergy treating-effective dose of a compound selected from the group consisting of those with the structure of type A:

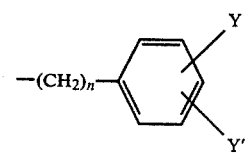

wherein

R° is hydrogen, alkyl of 1 to 6 carbon atoms, alkenyl of 3 to 6 carbon atoms, alkynyl of 3 to 6 carbon atoms, cycloalkyl of 3 to 6 carbon atoms, cycloalkylalkyl in which the cycloalkyl is of 3 to 6 carbon atoms and the alkyl portion is of 1 or 2 carbon atoms, or a group:

$$-(CH_2)_n-\phi_{Y,Y'}$$

in which n is 0 or 1,

Y and Y' are, independently, hydrogen, fluoro, chloro or bromo, alkyl of 1 to 3 carbon atoms, alkoxy of 1 to 3 carbon atoms or trifluoromethyl; provided that the unsaturation in any alkenyl or alkynyl is other than on the alpha carbon atom; and R and R' are independently hydrogen, fluoro or chloro, alkyl of 1 to 4 carbon atoms, alkoxy of 1 to 4 carbon atoms, nitro or trifluoromethyl; provided that only one of R and R' can be nitro or trifluoromethyl; or R and R' together form 6,7-methylenedioxy; and R'' is alkyl of from 1 to 4 carbon atoms or M, in which M is hydrogen or an equivalent of a cation which results in a salt which is pharmaceutically acceptable and those with the structure of type B:

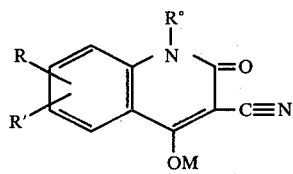

in which $R^o$, R, R' and M are as defined.

3. A method of claim 2 in which the daily dosage of the compound is from about 30 milligrams to about 600 milligrams.

4. A method of claim 2 in which the structure of the compound is of type A.

5. A method of claim 2 in which the structure of the compound is of type B.

6. A method of claim 2 in which $R^o$ of the compound is alkyl or alkenyl.

7. A method of claim 6 in which $R^o$ of the compound is allyl.

8. A method of claim 2 in which R and R' of the compound each are alkoxy.

9. A method of claim 8 in which R and R' of the compound represent 6,7-dialkoxy.

10. A method of claim 9 in which R and R' of the compound represent 6,7-dimethoxy.

11. The method of claim 2 in which the compound is 1-allyl-3-cyano-1,2-dihydro-4-hydroxy-6,7-dimethoxy-2-oxo-quinoline.

* * * * *